(12) United States Patent
Yamada et al.

(10) Patent No.: US 8,815,078 B2
(45) Date of Patent: Aug. 26, 2014

(54) PH OR CONCENTRATION MEASURING DEVICE AND PH OR CONCENTRATION MEASURING METHOD

(75) Inventors: Akira Yamada, Okayama (JP); Michihiro Nakamura, Okayama (JP); Satoshi Mohri, Okayama (JP); Keiji Naruse, Okayama (JP)

(73) Assignee: National University Corporation Okayama University (JP)

( * ) Notice: Subject to any disclaimer, the term of this patent is extended or adjusted under 35 U.S.C. 154(b) by 211 days.

(21) Appl. No.: 13/391,746

(22) PCT Filed: Aug. 24, 2010

(86) PCT No.: PCT/JP2010/064257
§ 371 (c)(1),
(2), (4) Date: Feb. 22, 2012

(87) PCT Pub. No.: WO2011/024793
PCT Pub. Date: Mar. 3, 2011

(65) Prior Publication Data
US 2012/0145563 A1  Jun. 14, 2012

(30) Foreign Application Priority Data
Aug. 25, 2009  (JP) ................................ 2009-194304

(51) Int. Cl.
*G01N 27/416*  (2006.01)
(52) U.S. Cl.
CPC .. *G01N 27/4167* (2013.01); *H01L 2924/13073* (2013.01)
USPC .................... 205/787.5; 422/68.1; 422/82.03; 204/416; 257/253
(58) Field of Classification Search
CPC ............. G01N 27/416; G01N 27/4167; H01L 2924/13073
USPC ........ 204/416; 205/787.5; 257/253; 324–438; 422/68.1, 82.01; 435/287.1
See application file for complete search history.

(56) References Cited

FOREIGN PATENT DOCUMENTS

| JP | 9-178697 A | 7/1997 |
| JP | 2005-127974 A | 5/2005 |
| JP | 2006-132989 A | 5/2006 |

OTHER PUBLICATIONS

Berg J., Dallas T.: Peristaltic Pumps. In: Li D. (Ed.) Encyclopedia of Microfluidics and Nanofluidics: SpringerReference (www.springer-reference.com). Springer-Verlag Berlin Heidelberg, 2008. DOI: 10.1007/SpringerReference_67432 May 14, 2013 04:21:18 UTC.*

(Continued)

*Primary Examiner* — Jennifer Dieterle
(74) *Attorney, Agent, or Firm* — Cantor Colburn LLP

(57) ABSTRACT

Disclosed are a pH or concentration measuring device and a pH or concentration measuring method which enable measurement in the shortest possible time even in an object to be measured having low buffer capacity. Specifically disclosed are a pH or concentration measuring device and measuring method for measuring the pH or concentration of a sample solution that is an object to be measured, the device being provided with first and second sensors that each output a signal corresponding to the pH or concentration of a solution, an inspection tube that is provided with a first room in which the first sensor is disposed and a second room in which the second sensor is disposed, a feeding means that feeds a baseline solution into the inspection tube, and an injecting means which injects the sample solution into the first room of the inspection tube and brings the sample solution into contact with the first sensor, wherein a vibration means which vibrates the interface between the sample solution stored in the first room and the baseline solution is provided.

6 Claims, 8 Drawing Sheets

(56) References Cited

OTHER PUBLICATIONS

JP 09-178697—machine translation performed Nov. 8, 2013.*
Mengnian et al. (IEEE, 1995).*
International Search Report for International Application No. PCT/JP2010/064257, mailed Nov. 2, 2010, with English translation.

Akira Yamada et al., "Automatic pH measurement using ISFET", Japan Society of Mechanical Engineers Conference on Robotic s and Mechatronics 2009 Koen Ronbunshu, May 24, 2009, p. 2A2-L04 (1)-(3).

* cited by examiner

PH OR CONCENTRATION MEASURING DEVICE AND PH OR CONCENTRATION MEASURING METHOD

CROSS REFERENCE TO RELATED APPLICATIONS

This is a U.S. national stage of application No. PCT/JP2010/064257, filed on 24 Aug. 2010. Priority under 35 U.S.C. §119(a) and 35 U.S.C. §365(b) is claimed from Japanese Application No. 2009-194304, filed 25 Aug. 2009, the disclosure of which is also incorporated herein by reference.

TECHNICAL FIELD

The present invention relates to a pH or concentration measuring device and a pH or concentration measuring method.

BACKGROUND ART

Conventionally, an ISFET (Ion Sensitive FET) is known which is a field effect transistor (FET) in which a predetermined ion sensitive membrane is provided in a gate part. The ISFET can detect the change of gate potential generated by the reaction of the ion sensitive membrane to a predetermined ion.

Such an ISFET is known which functions as a pH sensor by employing tantalum oxide ($Ta_2O_5$) membrane or the like as the ion sensitive membrane so as to detect hydrogen ions in a liquid (for example, see the Patent Literature 1). The ISFET can detect various ions by controlling the material of the ion sensitive membrane suitably and is used largely as a sensor for measuring concentration or the like.

A device is proposed which measures automatically a pH of a liquid with the pH sensor mentioned above (for example, see the Patent Literature 2).

The automatic pH measuring device includes a pH sensor probe composed of a measurement pH sensor, a reference pH sensor, and a pseudo reference electrode at a predetermined position. The measurement pH sensor, the reference pH sensor and the pseudo reference electrode are soaked in a baseline solution and detect baseline potential so as to perform calibration. Subsequently, by absorbing a sample solution that is an object to be inspected into the pH sensor probe, the measurement pH sensor contacts the sample solution and detects the potential thereof so as to detect hydrogen ion concentration, whereby pH is measured.

PRIOR ART REFERENCE

Patent Literature

Patent Literature 1: the Japanese Patent Laid Open Gazette Hei. 9-178697
Patent Literature 2: the Japanese Patent Laid Open Gazette 2005-127974

DISCLOSURE OF INVENTION

Problems to be Solved by the Invention

However, in the case in which the measurement pH sensor is constructed by an ISFET, for example in the case of pH measurement of a solution whose buffer capacity is lower than 0.2 mM/pH, as shown in FIG. 8, following start of measurement, large overshoot potential is generated between the measurement pH sensor and the reference pH sensor and the return thereof requires long time. Therefore, a measurement value of pH calculated with a final output at 65 seconds includes large error whose absolute value is 0.12 to 0.394 pH.

Especially, until the overshoot potential is disappeared, accurate measurement cannot be performed, whereby the time required for the measurement is very long and it is difficult to shorten the measurement time. In FIG. 8, the measurement is started at 6 seconds after the absorption of sample solution into the pH sensor probe. Six seconds is a time lag from the absorption of a sample solution that is an object to be inspected into the pH sensor probe to the contact of the sample solution to the measurement pH sensor. In this case, a potassium chloride solution of predetermined concentration is used as the sample solution. Especially, each sample solution contains such a low concentration of phosphates as 26 μM monopotassium phosphate, 108 μM dipotassium hydrogen phosphate so that the buffer capacity solution may be low; 0.06 mM/pH in the pH range from 6.5 to 6.6.

In consideration of the present status, the inventors performed research and development so as to measure a specimen of low buffer capacity as quickly as possible, whereby the present invention was obtained.

Means for Solving the Problems

A pH or concentration measuring device according to the present invention has first and second sensors each of which is constructed by an ISFET, an inspection tube whose tip side is provided therein with a first room in which a sample solution that is an object to be measured is held and whose basal side is provided therein with a second room in which a baseline solution is held, a feeding means feeding the baseline solution into the inspection tube from it's basal side, and an injecting means injecting the sample solution into the first room. The first sensor is housed in the first room as a measurement sensor. The second sensor is housed in the second room as a reference sensor. The inside of the inspection tube is washed by the baseline solution fed by the feeding means and subsequently the sample solution is injected into the first room by the injecting means so that the sample solution contacts the first sensor and the baseline solution contacts the second sensor, whereby a pH or concentration of the sample solution is measured. A vibration means is provided which vibrates an interface between the sample solution and the baseline solution formed in the inspection tube by injecting the sample solution into the first room.

Furthermore, in the pH or concentration measuring device according to the present invention, the vibration means vibrates the interface by applying pressure variation on the baseline solution stored in the second room, and the vibration means vibrates the interface at frequency not less than 0.1 Hz for 0.1 to 60 seconds.

In a pH or concentration measuring method according to the present invention, each of first and second sensors is constructed by an ISFET, and the first sensor contacts a sample solution that is an object to be measured and the second sensor contacts a baseline solution so as to measure a pH or concentration of the sample solution. The baseline solution is supplied to an inspection tube having a first room in which the first sensor is housed and a second room in which the second sensor is housed, and subsequently the sample solution is injected into the first room so as to form an interface between the sample solution and the baseline solution, and the measurement is performed after vibrating the interface.

Effect of the Invention

According to the present invention, in a measuring device and a measuring method measuring pH or concentration of a sample solution with a first sensor contacting the sample solution and a second sensor contacting a baseline solution, by vibrating an interface between the sample solution and the baseline solution, an overshoot potential generated between the first sensor and the second sensor is disappeared in a short time, whereby pH or concentration can be measured quickly. Accordingly, the measuring device and the measuring method which can measure pH or concentration with a short time are provided.

Figure 1:
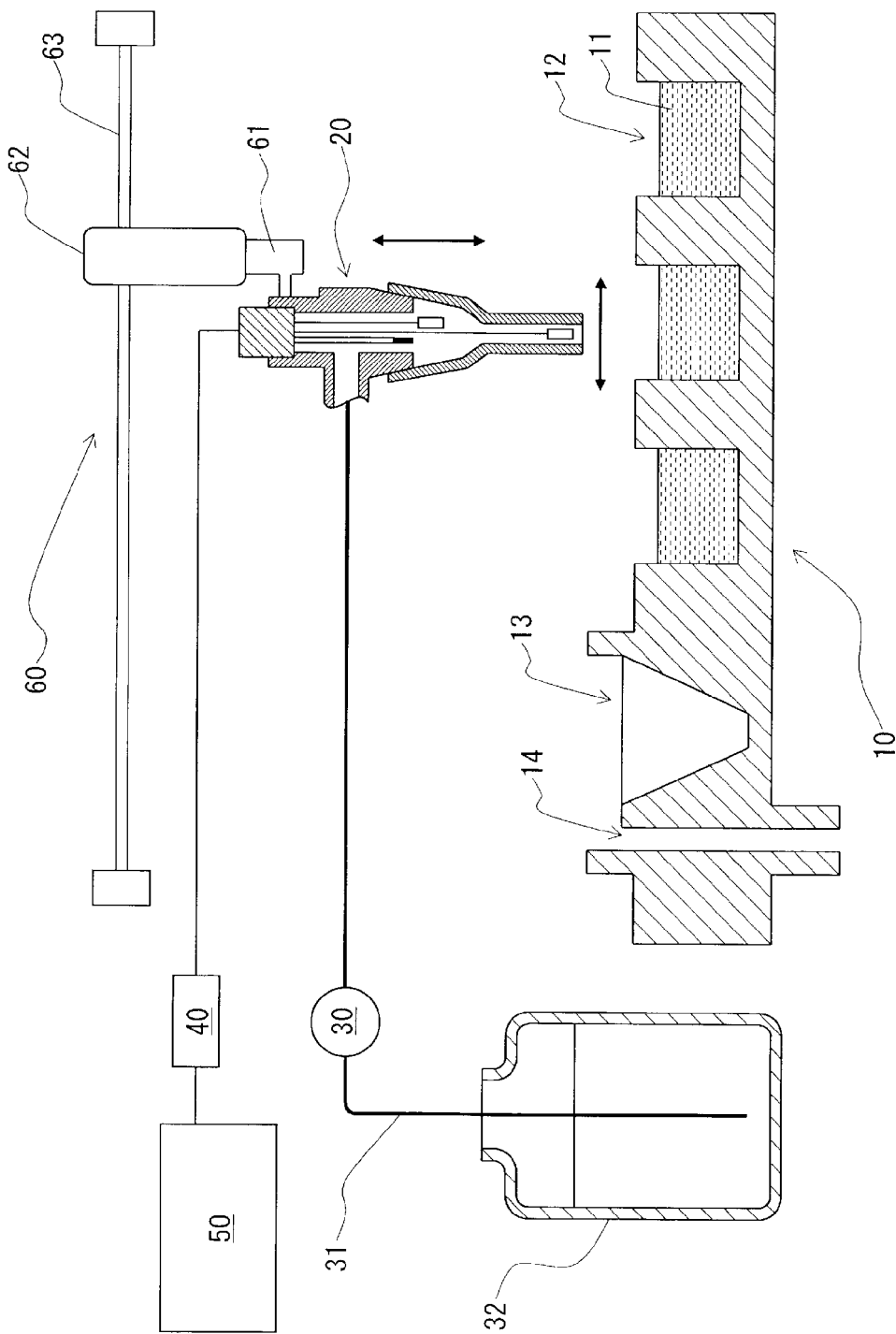
[FIG. 1] It is a schematic drawing of a pH or concentration measuring device according to an embodiment of the present invention.

DESCRIPTION OF NOTATIONS 10 microplate with sample wells
11 sample solution
12 sample well
13 discharge well
14 overflow pipe
20 inspection tube
21 connection part
22 first body of sensor probe
22a first flow path
22b second flow path
22c sealing body
23 second body of sensor probe
23a first room
23b second room
24 measurement pH sensor
25 reference pH sensor
26 pseudo reference electrode
30 pump
31 feeding pipe
32 solution tank
40 driving circuit
50 analytical unit
60 movement mechanism
61 rod
62 actuator
63 X-Y table
70 vibration mechanism
71 cylinder
72 piston
73 actuator
R interface

THE BEST MODE FOR CARRYING OUT THE INVENTION

In a pH or concentration measuring method according to the present invention, first and second sensors which output signals corresponding to pH or concentration of a solution, and the first sensor contacts a sample solution that is an object to be measured and the second sensor contacts a baseline solution, whereby the pH or concentration is measured with the signals output from the first and second sensors.

Especially, in the pH or concentration measuring method according to the present invention, an interface between the sample solution and the baseline solution formed when the first sensor is contacted the sample solution is vibrated by a suitable vibration means.

The inventors have known that an overshoot potential generated between the first sensor and the second sensor is disappeared in a short time by vibrating the interface between the sample solution and the baseline solution as mentioned above so as to enable measurement with a short time.

Explanation will be given on an embodiment of the present invention in detail below referring to drawings. FIG. 1 is a schematic drawing of a measuring device of the embodiment.

The measuring device of the embodiment is an automatic pH measuring device including a microplate 10 having a plurality of sample wells 12 in which sample solutions 11 are respectively stored, an inspection tube 20 which is a probe measuring pH by soaking its tip in the sample solutions 11, a pump 30 supplying a baseline solution from a solution tank 32 to the inspection tube 20 via a feeding pipe 31, a driving circuit 40 which supplies driving voltage for detecting pH and detects signals with sensors and electrodes provided in the inspection tube 20 as discussed later, an analytical unit 50 analyzing the signals detected by the driving circuit 40, and a movement mechanism 60 moving the inspection tube 20.

Figure 2:
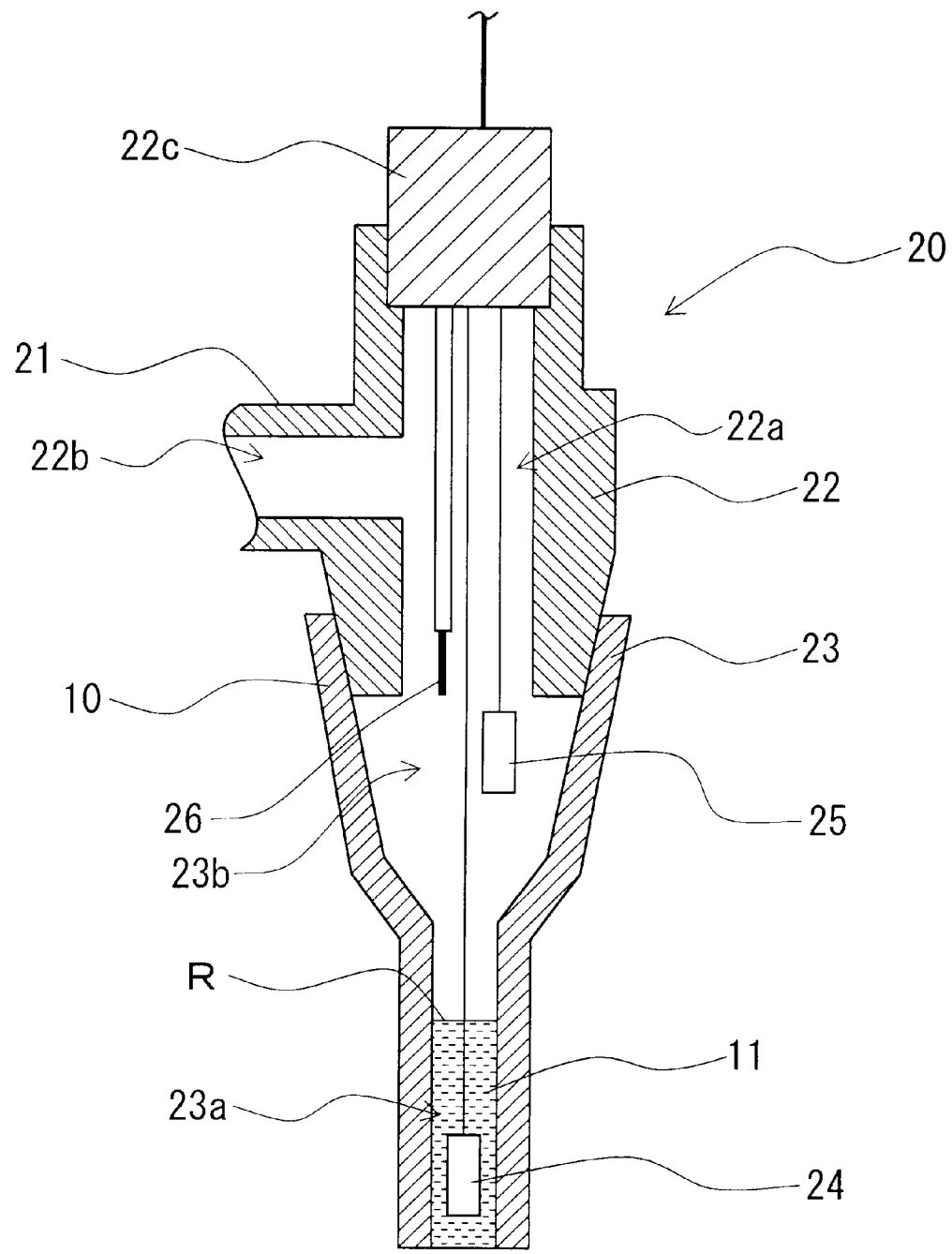
[FIG. 2] It is an explanation drawing of inspection tube.

As shown in FIG. 2, the inspection tube 20 includes a first body 22 having a connection part 21 to which one of the ends of the feeding pipe 31 is connected, a cylindrical second body 23 whose basal side is detachably attached to the first body 22 and whose tip side has smaller diameter than the basal side so as to make the whole second body 23 tapered, a measurement pH sensor 24 which is a first sensor provided inside the second body 23 and near the tip of the second body 23, a reference pH sensor 25 which is a second sensor provided inside the first body 22, and a pseudo reference electrode 26 provided near the reference pH sensor 25.

In FIGS. 1 and 2, for convenience of the explanation, the measurement pH sensor 24 and the reference pH sensor 25 are drawn large. However, actually, each of the measurement pH sensor 24 and the reference pH sensor 25 is a very small sensor whose width is about 0.5 mm, and is constructed by a pH-ISFET on the market.

The first body 22 is provided therein with a first flow path 22a penetratingly provided vertically and a second flow path 22b which penetrates the connection part 21 and connects communicatively one of its ends to the first flow path 22a and connects communicatively the other end to the feeding pipe 31, whereby the baseline solution supplied from the feeding pipe 31 is guided from the second flow path 22b to the first flow path 22a.

In the first body 22, a sealing body 22c is attached to an opening at the upper portion of the first flow path 22a so as to form a flow path substantially L-like shaped.

The second body 23 is detachably attached to the first body 22 by screwing the basal side of the second body 23 to the first body 22 so as to be connected to and communicated with the first flow path 22a, thereby guiding the baseline solution guided to the first flow path 22a into the second body 23.

Especially, since the second body 23 is tapered, the baseline solution is stored in the second body 23. In the second body 23, a part close to the end which is occupied by the sample solution 11 when the solution is absorbed and in which the measurement pH sensor 24 is provided is referred to as a first room 23a, and a part closer to basal end than the first room 23a is referred to as a second room 23b.

Each of the measurement pH sensor 24 and the reference pH sensor 25 constructed by a pH-ISFET is arranged at a predetermined position by regulating the length of the sensor wire fixed in the sealing body 22c.

The pseudo reference electrode 26 is also arranged near the reference pH sensor 25 by regulating the length of the wire fixed in the sealing body 22c.

In this embodiment, the part of the second body 23 close to the basal end is referred to as the second room 23b. However, the second room may be in the first body 22. The reference pH sensor 25 and the pseudo reference electrode 26 are arranged downstream the second flow path 22b so as to be soaked certainly in the baseline solution.

Wires taken out from the inspection tube 20 through the sealing body 22c is connected to the driving circuit 40. The driving circuit 40 drives the measurement pH sensor 24 and the reference pH sensor 25 and amplifies a potential difference between a potential of each of the measurement pH sensor 24 and the reference pH sensor 25 and a potential of the pseudo reference electrode 26 as an output signal, and inputs the potential difference into the analytical unit 50.

In this embodiment, the analytical unit 50 is an electronic computer such as a personal computer, and analyses the signals inputted from the driving circuit 40 so as to measure pH.

The analytical unit 50 controls the driving of the pump 30 which supplies the baseline solution to the inspection tube 20 and absorbs the sample solution 11, and the baseline solution is supplied to the inspection tube 20 based on the control of the analytical unit 50.

Furthermore, the analytical unit 50 also controls the movement mechanism 60 which moves the inspection tube 20. The movement mechanism 60 moves the inspection tube 20 vertically and laterally so as to measure pH of the sample solution 11 stored in the predetermined sample well 12 of the microplate 10 successively.

In this embodiment, the movement mechanism 60 includes an actuator 62 having a rod 61 moving vertically forward and rearward and a X-Y table 63 moving the actuator 62 horizontally. The tip of the rod 61 is equipped with the inspection tube 20. The movement mechanism 60 may be any form which can move the inspection tube 20 vertically and laterally.

The plurality of the sample wells 12 are provided in the microplate 10 and stores therein with the different sample solutions 11 respectively, and the inspection tube 20 is moved by the movement mechanism 60 and measures the sample solutions 11 continuously. A discharge well 13 is provided in the microplate 10 so as to wash the inspection tube 20.

As a sample vessel in which the sample solution is stored, a sample tube may alternatively be used instead of the microplate well 12. As the movement mechanism, a turntable may alternatively be used instead of the X-Y table.

Figure 3:
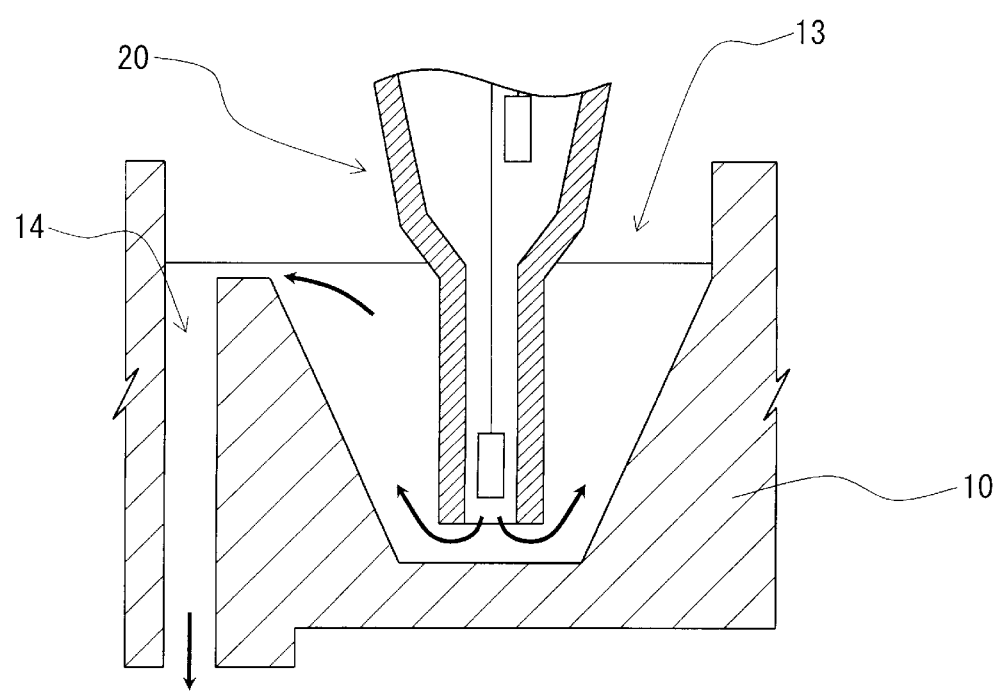
[FIG. 3] It is an explanation drawing of a washing step.

In the discharge well 13, as shown in FIG. 3, the pump 30 is driven while the tip of the inspection tube 20 has been inserted into the discharge well 13 so as to send the baseline solution from the tip of the inspection tube 20, whereby the inspection tube 20 and the measurement pH sensor 24 are washed with the baseline solution.

An overflow pipe 14 is provided in the discharge well 13, and the baseline solution and the sample solutions overflowed from the discharge well 13 are discharged via the overflow pipe 14.

In the case in which pH is measured with the measuring device constructed as mentioned above, firstly, as a washing step, the inspection tube 20 is washed by the discharge well 13. In the washing step, the inspection tube 20 is filled with the baseline solution, and each of the measurement pH sensor 24 and the reference pH sensor 25 contacts the baseline solution and outputs a corresponding signal. Based on the signals, zero point calibration is performed. At this time, the external wall of the tip of the inspection tube 20 to which the sample solution adheres is also washed.

Figure 4:
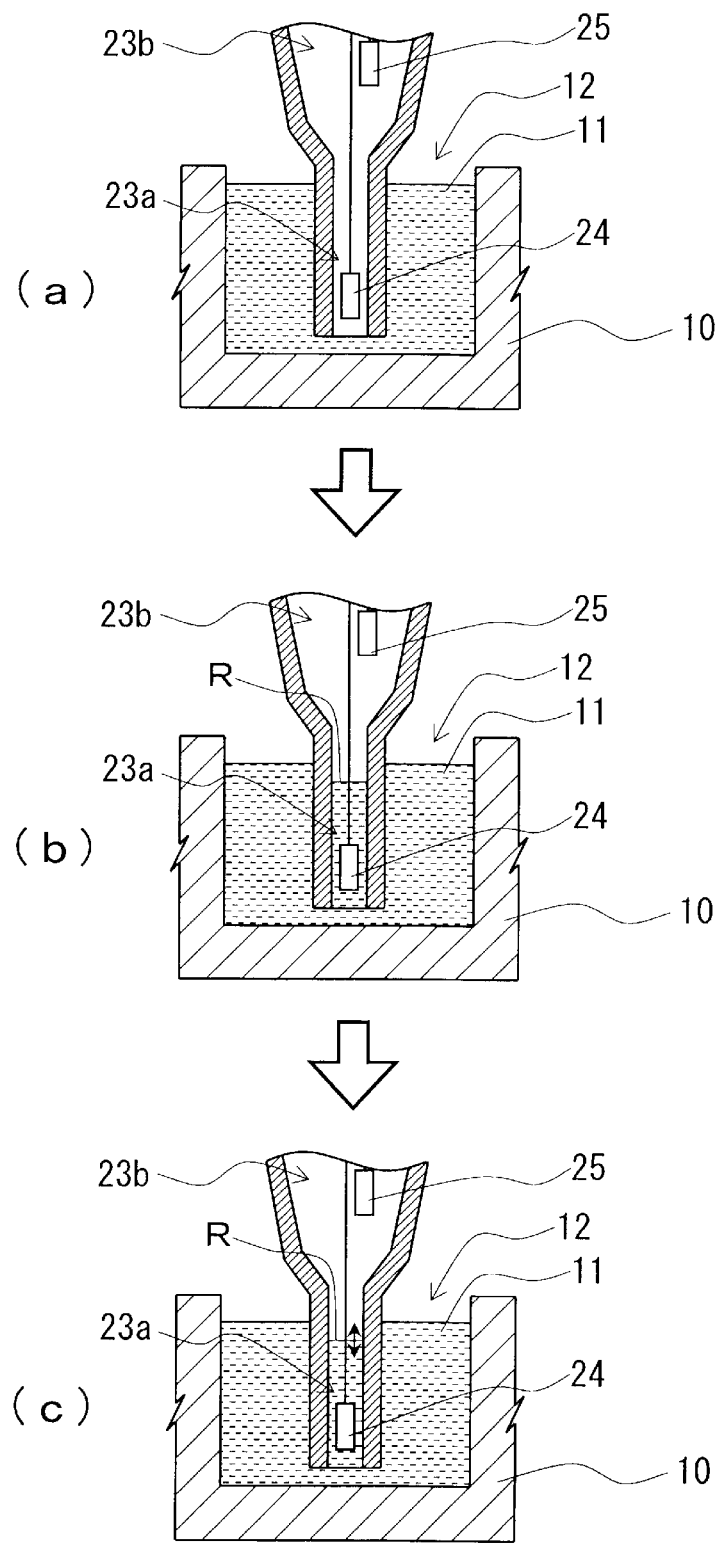
[FIG. 4] It is an explanation drawing of a measurement step.

Subsequently, as a measurement step, in the measuring device, the inspection tube 20 is moved by the movement mechanism 60 to the position above the predetermined sample well 12 and is moved downward so that the tip of the inspection tube 20 is soaked in the predetermined sample solution 11 as shown in FIG. 4(a). At this state, the pump 30 is driven reversely so as to make the baseline solution in the inspection tube 20 flow reversely, whereby, as shown in FIG. 4(b), the sample solution 11 is absorbed to the first room 23a of the inspection tube 20 and the sample solution 11 contact the measurement pH sensor 24.

Furthermore, in the measuring device, the forward driving and the reverse driving of the pump 30 are repeated alternately, whereby, as shown in FIG. 4(c), an interface R formed between the baseline solution in the inspection tube 20 and the sample solution 11 in the first room 23a is vibrated along arrows. In this embodiment, the pump 30 is used as a vibration means vibrating the interface R.

Especially, the pump 30 of the vibration means repeats the forward driving and the reverse driving alternately so as to apply pressure variation on the baseline solution in the second room 23b of the inspection tube 20, whereby the interface R can be vibrated very easily.

In the case of vibrating the interface R, during the vibration of the interface R, the measurement pH sensor 24 always contacts the sample solution 11 and the reference pH sensor 25 always contacts the baseline solution, whereby the interface R does not exceed over the positions of the measurement pH sensor 24 and the reference pH sensor 25.

Concretely, preferably, the vibration of the interface R is vibrated between the measurement pH sensor 24 and the reference pH sensor 25 with amplitude not more than 10% of the distance between the measurement pH sensor 24 and the reference pH sensor 25.

In this case, it is necessary for dissolving the overshoot potential to stir the sample solution 11 and the baseline solution near the interface R or to mix the sample solution 11 and the baseline solution following the vibration of the interface R. Mare vibration or reciprocal movement while the clear interface has been maintained is not effective for dissolving the overshoot potential.

The frequency of the vibrating interface R may be not less than 0.1 Hz and preferably about 1 to 100 Hz. The vibration time may be 0.1 to 60 seconds. In this embodiment, after absorbing the sample solution 11 to the first room 23a, the interface R is vibrated at about 2.0 Hz for about 30 seconds.

Figure 5:
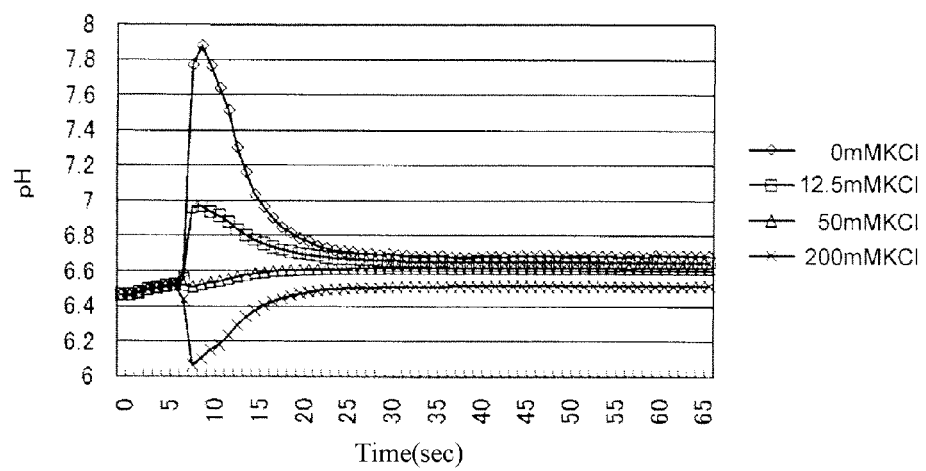
[FIG. 5] It is a graph of the time dependency of measurement data with the pH or concentration measuring device according to the present invention.
Figure 8:
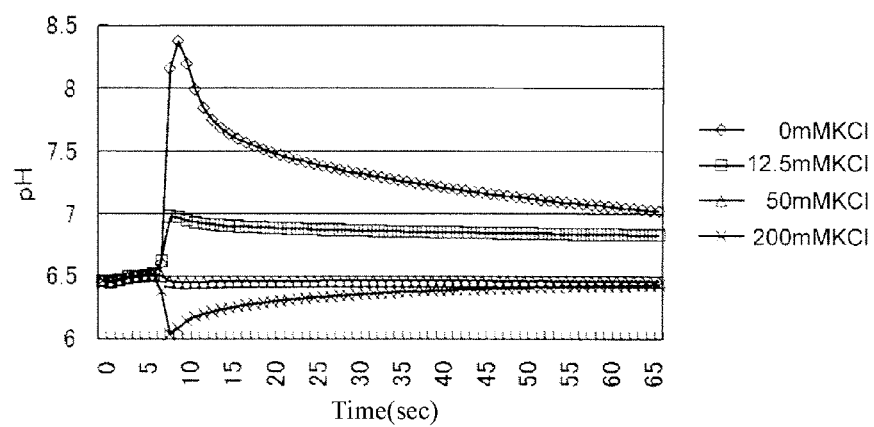
[FIG. 8] It is a graph of the time dependency of measurement data with a conventional pH or concentration measuring device.

As shown in FIG. 5, by vibrating the interface R, the overshoot potential generated following the start of measurement can be converged in a short time, whereby pH or concentration can be measured quickly. Therefore, a measuring device or method can be provided which can measure pH or concentration in a short time. In this case, as the sample solution 11, a potassium chloride solution of a predetermined concentration similar to the measurement shown in FIG. 8 was used. In this case, the absolute value of measurement error of pH is 0.010 to 0.060 pH and is widely improved in comparison with the case of FIG. 8.

In the case in which the interface R is vibrated by the pump 30 as mentioned above, the drive of the pump 30 should be controlled accurately, whereby the pump 30 may be expensive.

Figure 6:
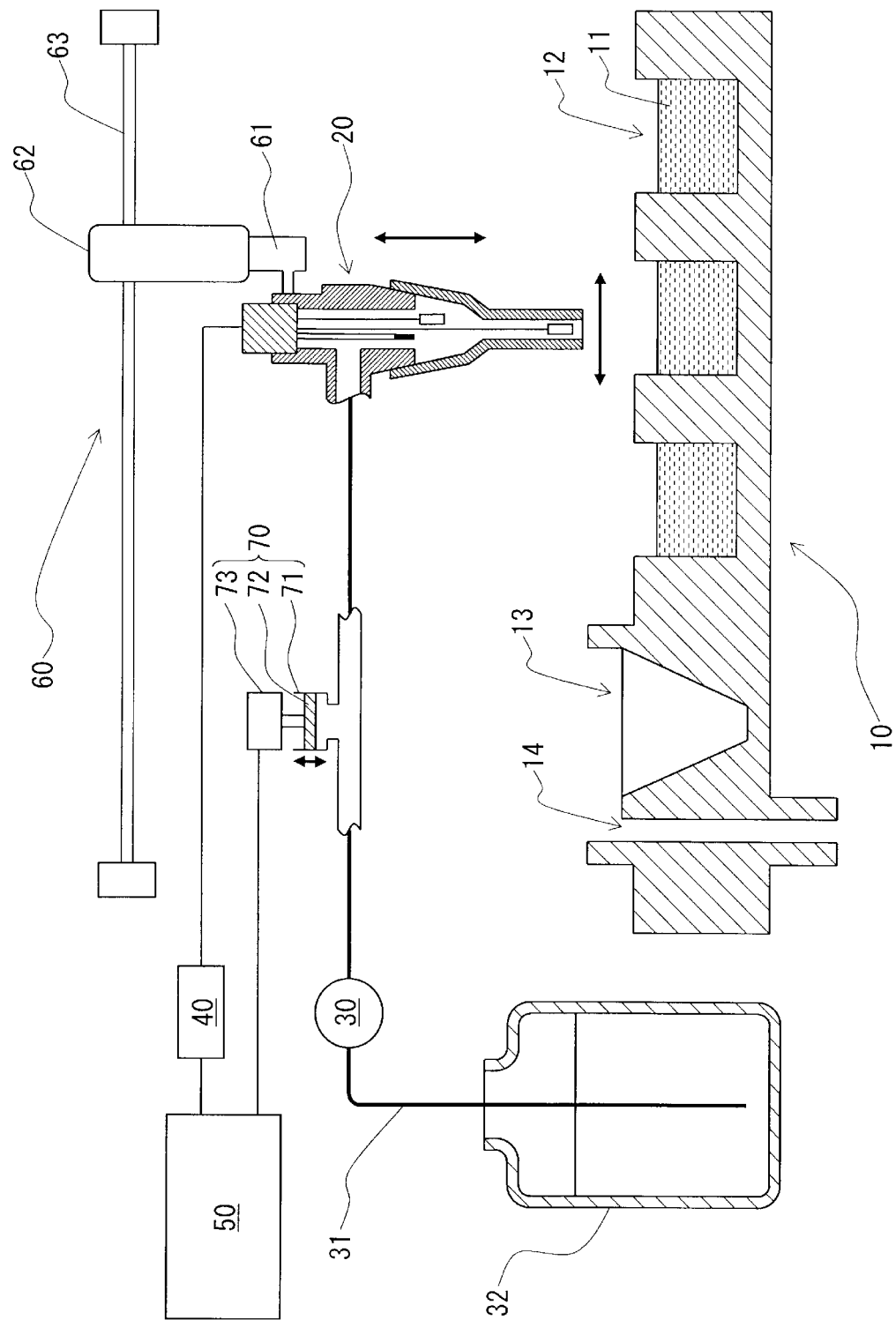
[FIG. 6] It is a schematic drawing of a pH or concentration measuring device according to another embodiment.

Accordingly, instead of reciprocating the baseline solution by the pump 30, a vibration mechanism 70 vibrating the interface R may alternatively be interposed in the feeding pipe 31 downstream the pump 30 as shown in FIG. 6.

The vibration mechanism 70 in this embodiment includes a cylinder 71 whose tip is communicated with and connected to the feeding pipe 31, a piston 72 provided in the cylinder 71, and an actuator 73 driving the piston 72 forward and rearward.

The vibration mechanism 70 may be used as the absorbing mechanism of the sample solution 11. Namely, the drive of the actuator 73 is controlled by the analytical unit 50, and the piston 72 is moved forward at the washing step and the piston 72 is moved rearward at the measurement step, whereby the sample solution 11 is absorbed to the first room 23a of the inspection tube 20.

According to the vibration mechanism 70 having the cylinder 71 and the piston 72, the amount of the sample solution 11 absorbed to the first room 23a can be controlled based on the amount of rearward movement of the piston 72, whereby the suction amount of the sample solution 11 can be controlled more accurately.

Furthermore, by vibrating the piston 72 at a predetermined amplitude and a predetermined frequency for a predetermined time by the actuator 73, predetermined pressure variation can be applied on the baseline solution stored in the second room 23b so as to vibrate the interface R between the sample solution 11 and the baseline solution.

According to the vibration mechanism 70 as mentioned above, the vibration of the interface R can be controlled easily. Furthermore, the pump 30 should only push the baseline solution along one direction, whereby the pump can be cheap. Therefore, the measuring device can be cheap.

The vibration mechanism 70 is not limited to the abovementioned form including the cylinder 71, the piston 72 and the actuator 73 and may alternatively be a suitable form which can apply predetermined pressure variation on the baseline solution stored in the second room 23b.

Figure 7:
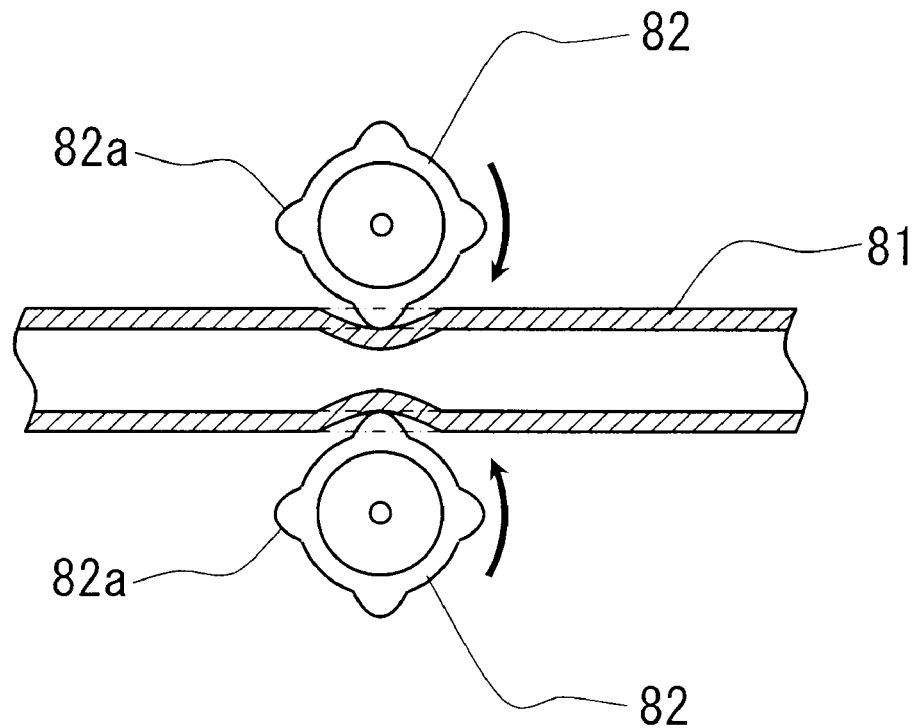
[FIG. 7] It is a schematic drawing of a vibration mechanism of another embodiment.

Namely, for example as shown in FIG. 7, a vibrating mechanism may alternatively be constructed by making a part of the feeding pipe 31 supplying the baseline solution with a flexible rubber pipe 81 and by providing two constriction cams 82 which pinch the rubber pipe 81 so as to constrict the rubber pipe 81 intermittently.

In this vibration mechanism, a driving motor (not shown) is provided so as to drive rotatively the constriction cams 82, and the driving of the motor is controlled by the analytical unit 50. The two constriction cams 82 are rotated oppositely to each other. A plurality of outward projections 82a are provided in the outer peripheral edge of each of the constriction cams 82 at predetermined intervals, whereby the rubber pipe 81 is constricted with the projections 82a by rotating the constriction cams 82.

Especially, in the two constriction cams 82 arranged oppositely to each other about the rubber pipe 81, the positions of the projections 82a are synchronized so that the projections 82a push the rubber pipe 81 simultaneously.

As mentioned above, in the case in which the part of the feeding pipe 31 supplying the baseline solution is constructed by the flexible rubber pipe 81 and the pressure variation is applied on the baseline solution in the rubber pipe 81 by constricting the rubber pipe 81 so as to vibrate the interface R between the sample solution 11 and the baseline solution, air is hardly gripped at the vibration mechanism, whereby the vibration mechanism can be operated stably.

The embodiment mentioned above is the pH measuring device in which each of the measurement pH sensor 24 and the reference pH sensor 25 is constructed by a pH-ISFET. However, by employing a measurement pH sensor and a reference pH sensor which can measure predetermined concentrations, a concentration measuring device may alternatively be constructed.

INDUSTRIAL APPLICABILITY

The present invention can be employed widely for a pH or concentration measuring device for various solutions.

The invention claimed is:

1. A pH or concentration measuring method comprising providing an inspection tube whose tip side is provided therein with a first room and whose basal side is provided therein with a second room;

locating a first sensor in the first room and a second sensor in the second room, wherein the first sensor is a measurement sensor, the second sensor is a reference sensor, and each of the first and the second sensors comprise an ion sensitive field effect transistor (ISFET);

feeding a baseline solution from the basal side of the inspection tube to the inside of the inspection tube so that the baseline solution contacts the second sensor; and injecting a sample solution, which is an object to be measured, into the first room so that the sample solution contacts the first sensor, and an interface is formed between the baseline solution and the sample solution, vibrating the interface between the sample solution and the baseline solution formed in the inspection tube by alternatively forward driving and reverse driving the baseline solution that is fed to the inspection tube.

2. A pH or concentration measuring device comprising:

an inspection tube whose tip side is provided therein with a first room in which a sample solution that is an object to be measured is stored, and whose basal side is provided therein with a second room in which a baseline solution is stored;

a first sensor located in the first room and a second sensor located in the second room, wherein the first sensor is a measurement sensor, the second sensor is a reference sensor, and each of the first and the second sensors comprise an ion sensitive field effect transistor (ISFET);

a feeding tube structured to feed the baseline solution from the basal side of the inspection tube to the inside of the inspection tube so that the baseline solution contacts the second sensor; and an injecting means structured to inject the sample solution into the first room so that the sample solution contacts the first sensor, and a vibration means structured to vibrate an interface between the sample solution and the baseline solution formed in the inspection tube by alternatively forward driving and reverse driving the baseline solution that is fed to the inspection tube.

3. The pH or concentration measuring device according to claim 2, wherein the vibration means vibrates the interface at frequency not less than 0.1 Hz for 0.1 to 60 seconds.

4. The pH or concentration measuring device according to claim 2, wherein the vibration means is structured to vibrate the interface between the first sensor and the second sensor with amplitude not more than 10 % of the distance between the first and the second sensor.

5. The pH or concentration measuring device according to claim 2, wherein the vibration means comprise a pump.

6. . The pH or concentration measuring device according to claim 2, wherein the vibration means comprise a cylinder whose tip is communicated with and connected to the feeding tube, a piston provided in the cylinder, and an actuator driving the piston forward and rearward.

* * * * *